(12) United States Patent
Aebi et al.

(10) Patent No.: US 6,712,825 B2
(45) Date of Patent: Mar. 30, 2004

(54) SPINAL DISC SPACE DISTRACTOR

(76) Inventors: Max Aebi, 687 Pine Avenue West, Montreal, Quebec (CA), H3A 1A1; Thomas Steffen, 373 Place D-Youville, Apt. 505, Montreal, Quebec (CA), H2Y 2B7; David C. Paul, 405 Greene La., Phoenixville, PA (US) 19460; William A. Cottle, 3951 West 20th Avenue, Vancouver, British Columbia (CA), V6S 1G3; Beat Schenk, Steinackerstrasse 14, Nugler (CH), 4412

( * ) Notice: Subject to any disclaimer, the term of this patent is extended or adjusted under 35 U.S.C. 154(b) by 287 days.

(21) Appl. No.: 09/880,000

(22) Filed: Jun. 14, 2001

(65) Prior Publication Data

US 2001/0031969 A1 Oct. 18, 2001

Related U.S. Application Data

(62) Division of application No. 09/411,161, filed on Oct. 1, 1999, now Pat. No. 6,261,296.
(60) Provisional application No. 60/102,669, filed on Oct. 2, 1998.

(51) Int. Cl.[7] .............................................. A61B 17/58
(52) U.S. Cl. ........................... 606/90; 606/61; 606/205; 600/219; 600/235
(58) Field of Search .............................. 606/53, 60, 61, 606/80, 99, 105, 190, 193, 205, 206, 207, 208; 600/201, 210, 219, 225, 235, 193, 196, 213

(56) References Cited

U.S. PATENT DOCUMENTS

| | | |
|---|---|---|
| 326,909 A | 9/1885 | Kricker |
| 430,331 A | 6/1890 | Ballard |
| 544,268 A | 8/1895 | Unsinger et al. |
| 1,359,164 A | 11/1920 | Lo Giudice |
| 1,465,905 A | 8/1923 | Hoff |
| 1,506,032 A | 8/1924 | Stevens |
| 1,553,623 A | 9/1925 | McLeod |
| 1,557,370 A | 10/1925 | Lane |
| 1,985,108 A | 12/1934 | Rush |
| 2,109,147 A | 2/1938 | Grosso |
| 2,507,710 A | 5/1950 | Grosso |
| 2,587,486 A | 2/1952 | Kogan |
| 2,595,989 A | 5/1952 | Smeltz .................... 43/53.5 |
| 2,687,661 A | 8/1954 | Richardson ................ 81/46 |
| 3,114,367 A | 12/1963 | Carpenter et al. |
| 3,557,792 A | 1/1971 | Rubin |
| 3,750,652 A | 8/1973 | Sherwin |

(List continued on next page.)

FOREIGN PATENT DOCUMENTS

| | | |
|---|---|---|
| SU | 680732 | 8/1979 |
| SU | 1101226 | 7/1984 |
| WO | WO 98/34552 | 8/1998 |
| WO | WO 99/45856 | 9/1999 |

OTHER PUBLICATIONS

Integra Neurosciences Corp., *Retractors*, available at http://www.integra–neurosciences.com/redmond–ruggles_index–.shtml, Jul. 26th, 2001.
Kapczynski, Helmut, *Surgical Instruments 101: An Introduction to KMedic Certified Instruments* at B52 (1997).
"Surgical Technique Using FRA Spacer Instruments—Technique Guide" by Synthese Spine (1998).
"AO AISF Principles in Spine Surgery," Chapter 9.3–Cage Systems, pp. 215–223.

*Primary Examiner*—David O. Reip
(74) *Attorney, Agent, or Firm*—Jones Day

(57) ABSTRACT

A distractor for separating adjacent elements, such as vertebrae. The distractor preferably has a scissors-type distracting mechanism, either in a simple scissors or double-acting scissors configuration. The distractor includes blades that are removable from the jaws of the distractor such that different blades may be used depending on the patient and situation with which the distractor is to be used. The jaws include a mating fixture and the blades include a mating portion for removable association with the mating fixture.

30 Claims, 9 Drawing Sheets

U.S. PATENT DOCUMENTS

| | | | |
|---|---|---|---|
| 3,916,907 A | 11/1975 | Peterson | |
| 4,050,464 A | 9/1977 | Hall | |
| 4,545,374 A | 10/1985 | Jacobson | |
| 4,554,848 A | 11/1985 | Galletto | 81/447 |
| D291,729 S | 9/1987 | Greig | D24/27 |
| 4,754,746 A | 7/1988 | Cox | |
| 4,827,929 A | 5/1989 | Hodge | |
| 4,896,661 A | 1/1990 | Bogert et al. | 606/86 |
| 4,898,161 A | 2/1990 | Grundei | 606/105 |
| D307,322 S | 4/1990 | Dolwick | D24/10 |
| 4,997,432 A | 3/1991 | Keller | 606/61 |
| 5,019,081 A | 5/1991 | Watanabe | 606/79 |
| 5,021,056 A | 6/1991 | Hofmann et al. | 606/86 |
| 5,059,194 A | 10/1991 | Michelson | 606/61 |
| 5,122,130 A | 6/1992 | Keller | 606/61 |
| 5,209,755 A | 5/1993 | Abrahan et al. | 606/132 |
| 5,213,112 A | 5/1993 | Niwa et al. | 128/774 |
| 5,234,460 A | 8/1993 | Stouder, Jr. | 606/205 |
| 5,281,223 A | 1/1994 | Ray | 606/61 |
| 5,297,538 A | 3/1994 | Daniel | 128/20 |
| 5,363,841 A | 11/1994 | Coker | 128/20 |
| 5,368,596 A | 11/1994 | Burkhart | 606/79 |
| 5,395,370 A | 3/1995 | Muller et al. | 606/61 |
| 5,415,659 A | 5/1995 | Lee et al. | 606/61 |
| 5,423,826 A | 6/1995 | Coates et al. | 606/96 |
| 5,431,658 A | 7/1995 | Moskovich | 606/99 |
| 5,529,571 A | 6/1996 | Daniel | 600/219 |
| 5,584,831 A | 12/1996 | McKay | 606/61 |
| 5,630,821 A | 5/1997 | Klaas | 606/107 |
| 5,676,666 A | 10/1997 | Oxland et al. | 606/61 |
| 5,697,889 A | 12/1997 | Slotman et al. | 600/204 |
| 5,704,937 A | 1/1998 | Martin | 606/61 |
| 5,725,532 A | 3/1998 | Shoemaker | 606/96 |
| 5,931,777 A | 8/1999 | Sava | 600/213 |
| 5,993,385 A * | 11/1999 | Johnston et al. | 600/213 |
| 6,017,342 A | 1/2000 | Rinner | 606/57 |
| 6,080,162 A | 6/2000 | Dye et al. | 606/80 |

* cited by examiner

SPINAL DISC SPACE DISTRACTOR

CROSS-REFERENCE TO RELATED APPLICATION

This application is a divisional of copending U.S. patent application Ser. No. 09/411,161, filed Oct. 1, 1999, now U.S. Pat. No. 6,261,296, which claims priority to U.S. Provisional Application No. 60/102,669, filed Oct. 2, 1998.

FIELD OF THE INVENTION

The present invention relates to a device and method for spreading apart adjacent vertebrae of a vertebral column so that an implant may be inserted therebetween. More particularly, the present invention relates to a distractor device shaped and configured for minimally invasive insertion and use, such as for distraction of vertebrae using an anterior or anterolateral approach.

BACKGROUND OF THE INVENTION

Back pain can be caused by either one or a combination of the following: a loss of disc height, compression of nerve roots, degenerative disc disease, spondylolisthesis, and other causes. The current standard of treatment for people suffering from severe back pain requiring surgical intervention due to different types of pathology is by intervertebral fusion. Intervertebral fusion is achieved by fusing two adjacent vertebral bodies together by removing the affected disc and inserting a suitably sized implant into the disc space that allows for bone to grow between the two vertebral bodies bridging the gap left by the disc removal.

Known intervertebral fusion procedures typically involve the steps of removing a portion or all of the affected disc material, spreading apart adjacent vertebrae with a distractor, and inserting an implant into the space previously occupied by the removed disc material. This procedure can be done either from the front of the patient (anterior interbody fusion) or from the back (posterior interbody fusion). If done from the front, it is important to reduce the size of the distractor so that the procedure is as minimally invasive as possible and thus minimally interferes with and traumatizes the organs and vasculature between the vertebral region being treated and the insertion point. Posterior fusion can utilize larger implants and tools since the insertion space is more accommodating.

Current implants used for interbody fusion include allograft rings/dowels and cages such as threaded cages. However, the technique for the insertion of these implants generally does not achieve distraction because of their height limitations, thus making it difficult to restore the natural disc height. The force necessary to insert these implants (such as by drilling and tapping) may cause damage to the vertebrae or vertebral endplates at the insertion site. Moreover, allograft products and cages made out of other brittle materials (e.g., carbon fiber and ceramics) may break during insertion, particularly when distraction is not used and external force is necessary to insert the implant. Threaded cages on the other hand do not restore lordosis, and do not allow for atraumatic distraction to restore disc height. Thus, there remains a need for improvements in this area.

SUMMARY OF THE INVENTION

In accordance with the principles of the present invention, a spinal disc distractor is provided to allow for an implant insertion technique to be performed during distraction of the disc space. The implants are slid into the disc space between the distractor blades, preferably while the blades are in contact with the upper and lower surfaces of the adjacent vertebral bodies. The distractor of the present invention is formed to be as minimally invasive and atraumatic as possible such that it may readily be used in an anterior or anterolaterial approach. Thus, the distractor of the present invention is configured to be used in the confined spaces of the human anatomy through a small surgical incision and permits the use of laparoscopic approaches like Balloon Assisted Endoscopic Retroperitoneal Gasless ("BERG").

In a preferred embodiment, the distractor of the present invention has a scissor-like configuration with a pair of handles pivotally connected together. A distractor jaw is coupled to a distal end of each handle such that movement of the handles together draws the jaws apart to separate the vertebrae being treated. In an even more preferred embodiment, the jaws and handles are pivotally coupled together in a double-acting scissor-like configuration to further reduce the space required to move the jaws apart and thus further minimize the invasiveness of the device and procedure.

Although the handles, jaws, and distractor mechanism of the present invention may all lie in the same plane, in order to facilitate visualization of the treatment site during distraction and insertion of an implant, at least the handles may be angled away from the plane of the distractor jaws. In a preferred embodiment, the distractor mechanism is angled downwardly with respect to the jaws and the handles are angled downwardly with respect to the distractor mechanism to further enhance visualization and also to permit greater space for the implant holder adjacent the proximal end of the distractor during insertion of the implant.

A locking mechanism preferably is provided adjacent to or in the handle to maintain distraction. The locking mechanism may include a spindle or threaded bolt mounted on a first handle and passing through the second handle. An internally threaded speed nut is rotatably mounted on the threaded bolt such that movement of the speed nut along the bolt selectively inhibits movement of the second handle away from the first handle and thus maintains the vertebrae at the desired distracted position.

The blades of the distractor of the present invention are configured to increase versatility of the distractor. In a first embodiment of the present invention, the blades are removably coupled to the distractor jaws. Thus, the blades may be changed, as necessary or desired, for a given procedure or patient.

In another embodiment, the blades of the distractor are gradually curved to be out of the plane of the distractor mechanism. Because of the gradual curve, the distal end of the jaws may safely be manipulated through the patient's body with as minimal contact as possible with organs and vasculature including major blood vessels such as the vena cava and aorta. Moreover, such curvature permits insertion through a smaller incision because of the increased manipulability of the gradually curved blades through small openings and spaces.

In yet another embodiment, the blades of the distractor are configured to permit insertion of any type of implant. In particular, although certain implants may be provided with slots for engagement with a surface of the distractor blades during insertion, other implants do not have such slots. The blades of the third embodiment of the present invention are configured and sufficiently spaced apart to permit insertion of either type of implant, regardless of whether slots are provided for engaging distractor blades.

The spinal disc distractor of the present invention is thus designed to distract disc space atraumatically with respect to both the vertebrae and the implant during endplate preparation, implant sizing, and implant insertion. The distractor may be used in a straight anterior, anterolateral, or lateral approach, and may be used in either an open or a laparoscopic procedure. Moreover, the distractor is designed to ensure the selection of an anatomically correct implant size by permitting the annulus to be fully stretched so that the largest possible implant may be inserted and compressed upon release of the vertebrae, thereby enhancing stability and assuring correct placement of the implant. Thus, the present invention permits disc height and lordosis to be restored. The jaws are shaped and configured to preserve the endplate and the vertebral body during distraction, as well as to permit insertion of an implant during distraction. The risk of breakage of allograft implants and other cages made from brittle materials during insertion is thereby reduced.

BRIEF DESCRIPTION OF THE DRAWINGS

The detailed description will be better understood in conjunction with the accompanying drawings, wherein like reference characters represent like elements, as follows.

DETAILED DESCRIPTION OF THE INVENTION

Figure 1:
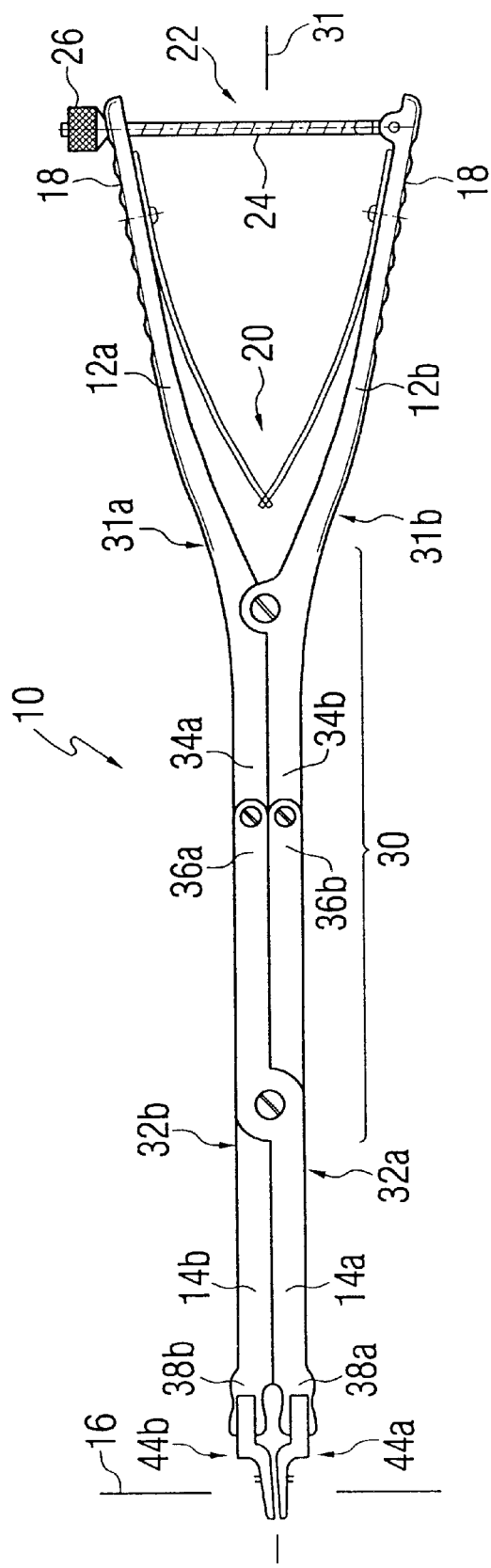
FIG. 1 is a top elevational view of a distractor with removable blades formed in accordance with the principles of the present invention.

In accordance with the principles of the present invention, a distractor 10 is provided with a pair of handles 12a, 12b movable with respect to each other to actuate a pair of jaws 14a, 14b coupled thereto, as shown in FIG. 1. Although distractor 10 may be used for a variety of procedures, a preferred procedure for which distractor 10 is used is spinal disc distraction. Thus, distractor 10 is preferably configured such that actuation of handles 12 (12a, 12b) moves jaws 14 (14a, 14b) apart substantially along distraction axis 16 to a working position corresponding to the desired resulting relative position of the endplates. For example, the blades may be moved to a substantially parallel or lordotic position to separate adjacent vertebrae to be treated.

In order to be optimally useful for use in an anterior approach, handles 12 and jaws 14 are configured to move jaws 14 apart along distraction axis 16 a sufficient amount to adequately separate adjacent vertebrae to be treated (typically 5 mm–20 mm, most typically 13 mm–15 mm) yet to occupy a minimal amount of space within the insertion region during the procedure. Thus, handles 12 and jaws 14 preferably are pivotally coupled together in a scissors configuration such that movement of handles 12a and 12b together causes jaws 14a and 14b to move apart and effect distraction of vertebrae between which jaws 14 are positioned. Thus, proximal ends 18 of handles 12 are configured to facilitate gripping. In a preferred embodiment, the outer surface of handle proximal ends 18 are contoured to increase user comfort, as shown in FIG. 2.

A biasing element 20, such as a pair of leaf springs, maintains handles 12a, 12b in a spaced apart configuration such that jaws 14a, 14b are close together, ready for insertion through a small incision and narrow passage through the patient in the neutral configuration of FIG. 1. A locking mechanism 22 is provided to counteract biasing element 20 as desired, such as to maintain jaws 14 at a desired spaced apart position for operation on the distracted vertebral region. Locking element may be in any desired configuration, such as a threaded bolt 24 coupled (typically pivotally) to one handle and slidably passing through the other handle, and a locking nut 26 threadedly and rotatably mounted on the end of bolt 24 extending past the other handle (i.e., the portion not between handles 14). Movement of nut 26, as a result of rotation, along bolt 24 thus shortens the length of bolt 24 between handles 14 and prevents the handles from moving apart, thus maintaining handles 12 in a position closer together than the neutral position.

A distractor mechanism 30 is provided such that movement of handles 12 to actuate distractor mechanism 30 causes jaws 14 to move apart to effect distraction of adjacent elements such as vertebrae. Distractor mechanism 30 may have a simple scissors configuration (such as in FIGS. 14–16 described below) such that handle 12a and jaw 14a are at opposite ends of a first lever arm and handle 12b and jaw 14b are on opposite ends of a second lever arm pivotally coupled to the first lever arm. In a preferred embodiment, distractor mechanism 30 is in the form of a double-acting scissor configuration having greater than one pivot point, thus reducing the amount of space required along distraction axis 16 and laterally away from distractor mechanism longitudinal axis 31 to effectuate distraction. As may be appreciated with reference to FIGS. 1 and 3, in order to form a double-acting scissor configuration, handles 12 and jaws 14 are provided on separate lever arms which are pivotally coupled together. In particular, handle 12a is formed at a proximal end of proximal lever arm 31a, handle 12b is formed at a proximal end of lever arm 31b, jaw 14a is formed at a distal end of distal lever arm 32a, and jaw 14b is formed at a distal end of distal lever arm 32b. Distal end 34a of proximal lever arm 31a is pivotally coupled to proximal end 36a of distal lever arm 32a and distal end 34b of proximal lever arm 31b is pivotally coupled to proximal end 36b of distal lever arm 32b. In order to actuate the double-acting mechanism to effectuate distraction and hence movement of jaws 14a, 14b apart upon movement of handles 12a, 12b together, one set of lever arms is laterally pivotally coupled together and the other set of lever arms is crosswise pivotally coupled together. In distractor mechanism 30 of FIGS. 1 and 3, proximal lever arms 31a, 31b are laterally pivotally coupled together and distal lever arms 32a, 32b are crossed over each other and pivotally coupled together. However, it will be appreciated that, instead, proximal lever arm 31a, 31b may be crossed-over each other and distal lever arms 32a, 32b may be laterally pivotally coupled. The double-acting configuration breaks the pivoting action into two components, reducing the total movement of distractor mechanism 30 required along distraction axis 16.

Figure 2:
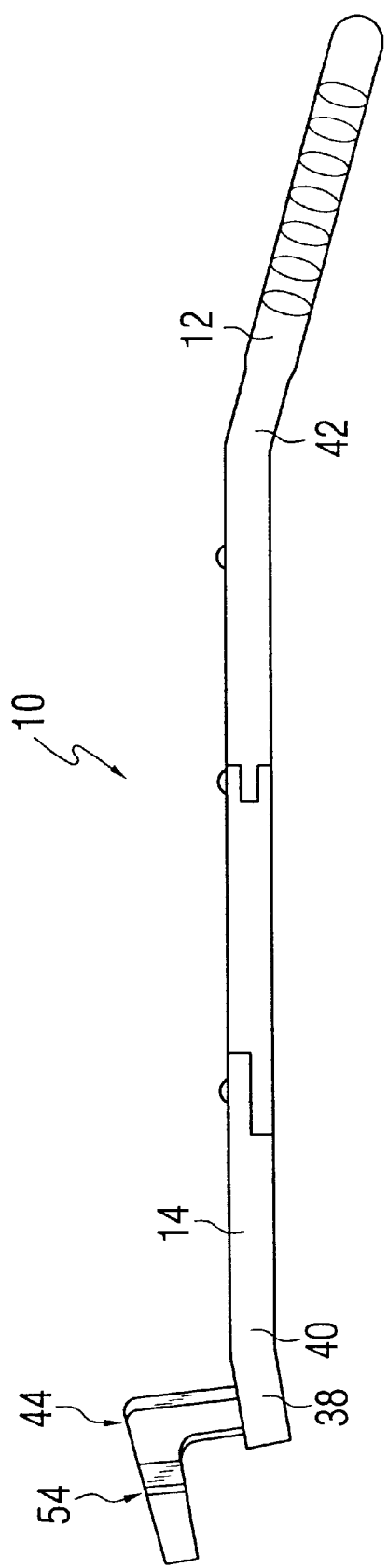
FIG. 2 is a side elevational view of the distractor of FIG. 1.

An additional feature of distractor 10 which facilitates use thereof during distraction is the relative offset positions of jaws 14a, 14b, handles 12a, 12b, and distractor mechanism 30 with respect to one another, as may be appreciated in the side elevational view of FIG. 2. In particular, in a preferred embodiment, distal jaw ends 38a, 38b are to be positioned to properly distract adjacent vertebrae and distractor mechanism 30 and handles 12a, 12b are offset relative to distal jaw ends 38a, 38b to permit optimal visualization of distal jaw ends 38a, 38b from the proximal end of distractor 10 (outside the patient's body) during distraction. For example, a distal bend 40 may be provided immediately proximal of distal jaw ends 38a, 38b, as may be appreciated with reference to FIG. 2. Thus, the remainder of distractor 10 (i.e., the proximal portions of distractor 10 such as distractor mechanism 30 and handles 12a, 12b) is in a different plane from the plane of distal jaw ends 38a, 38b and the distraction site. With such an offset, visualization of the distraction site and of insertion of the implant therein is enhanced. Additionally or alternatively, a proximal bend 42 may be provided immediately distal of handles 12a, 12b such that proximal handle ends 18a, 18b are not in the same plane as distal jaw ends 38a, 38b and the distraction site. The provision of either or both of bends 40, 42 causes at least a proximal portion of distractor 10 to be in a plane different from the plane of distal jaw ends 38a, 38b and the distraction site such that the line of site to view distraction is not obstructed by the distractor. Moreover, such offset of portions of distractor 10, such as distractor mechanism 30 and handles 12a, 12b, from the distal jaw ends 38 accommodate an implant holder for insertion of the implant to permit a substantially straight insertion of the implant holder. Bend 40 may be between 0°–30°, most preferably 10°, and bend 42 may be between 0°–30°, most preferably 15°, to achieve the desired improved visualization and increased area for the implant holder.

A distractor provided in accordance with the principles of the present invention is configured to distract adjacent vertebrae so that an implant may be inserted therebetween. Preferably, each jaw of a distractor formed in accordance with the principles of the present invention is provided with a blade shaped and configured to contact a vertebral endplate and also to permit insertion of an implant therebetween. Once the implant is properly positioned between the vertebral endplates, the distractor, along with its blades, may be removed from the distraction site in the patient.

Figure 3:
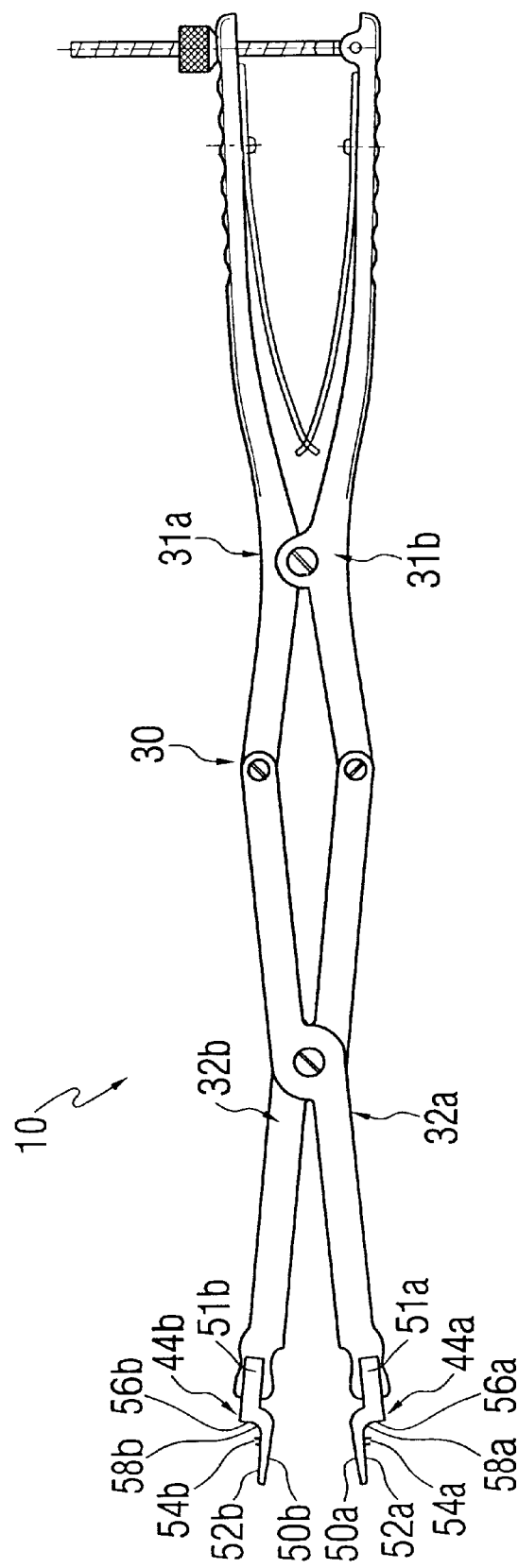
FIG. 3 is a top elevational view of the distractor of FIG. 1 in a working configuration with the jaws separated for distraction.
Figure 4:
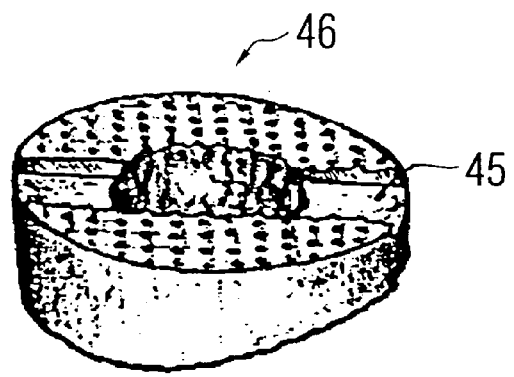
FIG. 4 is a perspective view of a femoral ring implant which may be used with a distractor formed in accordance with the principles of the present invention.
Figure 5:
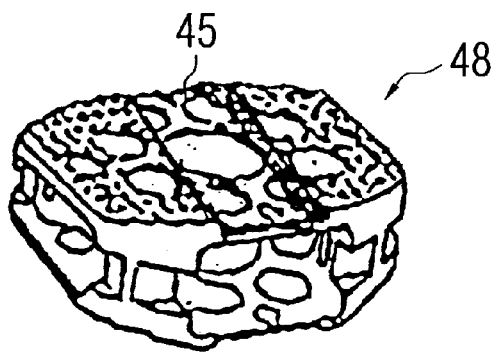
FIG. 5 is a perspective view of a cage implant which may be used with a distractor formed in accordance with the principles of the present invention.

In the embodiment of FIGS. 1–3, blades 44a, 44b are provided on jaws 14a, 14b, respectively, to engage the vertebrae to be distracted. In a preferred embodiment, blades 44a, 44b are configured and shaped to correspond to a slot 45 in an implant such as cage 46 of FIG. 4 or femoral ring 48 of FIG. 5. Thus, as the selected implant is moved toward the treatment site with a desired insertion tool, implant contacting surfaces 50a, 50b (FIG. 3) of blades 44a, 44b contact respective slots 45. Preferably, implant contacting surfaces 50a, 50b of blades 44a, 44b are closer together than the point of connection 51a, 51b of blades 44a, 44b to respective jaws 14a, 14b. Thus, jaws 14a, 14b are sufficiently spaced apart to permit insertion of the thickest dimension of the implant therebetween, yet blades 44a, 44b are closer together to account for the narrower dimension of the implant in the region of slots 45 and thereby to securely grasp the implant via slots 45.

Blades 44 may converge toward each other in a distal direction before actuation of distractor mechanism 30 as may be appreciated with reference to FIG. 1. Thus, upon actuation of distractor mechanism 30 and pivoting apart of jaws 14, blades 44, and particularly outwardly facing distracting surfaces 52a, 52b (positioned to contact the endplates in the treatment site), may be moved into an orientation appropriate for the vertebral region being treated. For example, actuation of distractor mechanism 30 may move distracting surfaces 52a, 52b into a parallel orientation with respect to each other to securely engage endplates which are parallel with respect to each other.

Figure 6:
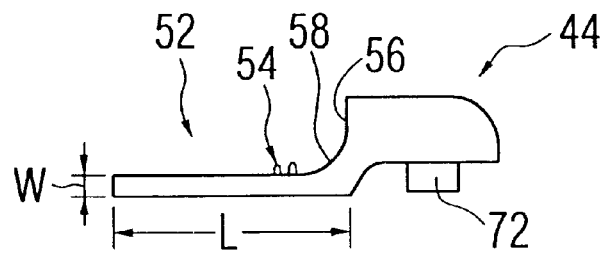
FIG. 6 is an isolated top elevational view of the blade of the distractor of FIG. 1.

Distracting surfaces 52a, 52b of blades 44a, 44b preferably are shaped to securely engage the vertebrae being treated, particularly the endplates thereof. In a preferred embodiment, distracting surfaces 52a, 52b are configured to securely engage the anterior lip of the vertebral endplates being treated, as shown in the isolated view of blade 44 in FIG. 6. For instance, distracting surfaces 52a, 52b may be provided with vertebral engagers 54a, 54b (FIGS. 2 and 6), such as in the form of ridges, which engage the endplates. Transverse engagement walls 56a, 56b (FIGS. 2 and 6) may be spaced from vertebral engagers 54a, 54b such that an anterior lip of the vertebral endplates fits therebetween. Engagement surface 58a, 58b (FIGS. 2 and 6) between vertebral engagers 54a, 54b and engagement walls 56a, 56b preferably is curved to accommodate the anterior lip of the vertebral endplates as well as to provide a smooth transition from distracting surfaces 52a, 52b to transverse engagement walls 56a, 56b.

Figure 7:
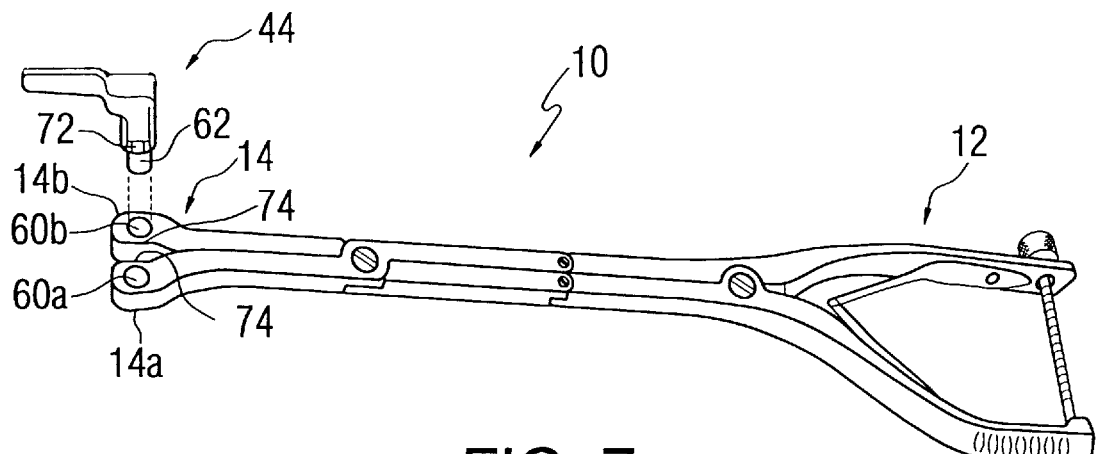
FIG. 7 is a perspective exploded view of the distractor of FIG. 1.
Figure 8:
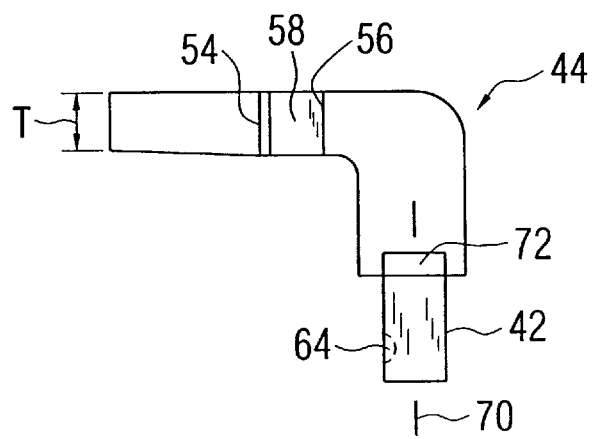
FIG. 8 is a side elevational view of the blade of the distractor of FIG. 1.
Figure 9:
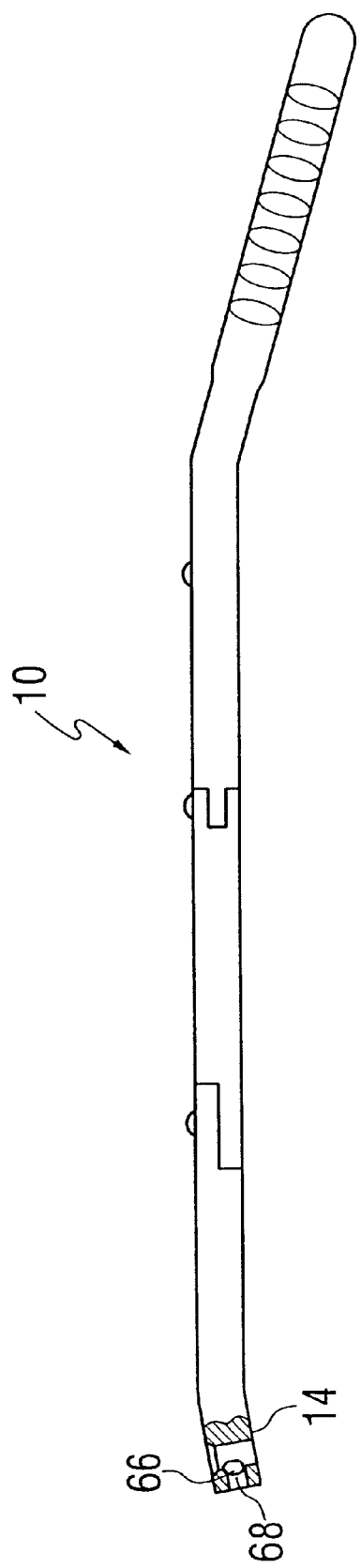
FIG. 9 is a side elevational view partially in cross-section of the distractor of FIG. 1 with the blade removed.

In accordance with the principles of the present invention, the distractor blades preferably are configured to increase versatility of use of the distractor of the present invention. It will be appreciated that distractor 10 preferably is formed from a surgical grade sterilizable metal such that the same distractor may be used for different patients. In order to increase the versatility of distractor 10 and its usefulness for different patients and situations, at least one of blades 44a, 44b may be removably coupled to its respective jaw 14a, 14b, as illustrated in FIG. 7. Thus, in such embodiment, jaws 14a, 14b are provided with a socket 60a, 60b shaped to receive a mounting post 62 of a blade 44, as shown in FIGS. 7 and 8. Post 62 may be releasably held within a bore 60 of a jaw 14 in any desired manner. For example, a ball detent attachment may be formed by providing a depression 64 in post 62 (FIG. 8) for matingly receiving a biased detent ball 66 housed within a transverse bore 68 in jaw 14 (FIG. 9). Blade post 62 preferably is fitted within socket 60 to permit pivotable movement of blade 44 about longitudinal axis 70 of blade post 62. Such pivotable movement facilitates manipulation of blade 44 with respect to the vertebral endplates to ease removal of blade 44 and distractor 10. If desired, in order to limit the range of pivotal motion of blade 44, a stop plate 72 (FIGS. 6–8) may be provided on post 62 to fit within range limiting groove 74 (FIG. 7) in jaw 14. Stop plate 72 extends transversely from post 62, as may be appreciated with reference to FIG. 6 and has stop surfaces 76a, 76b engaging respective range limiting surfaces 78a, 78b of range limiting groove 74.

Figure 10:
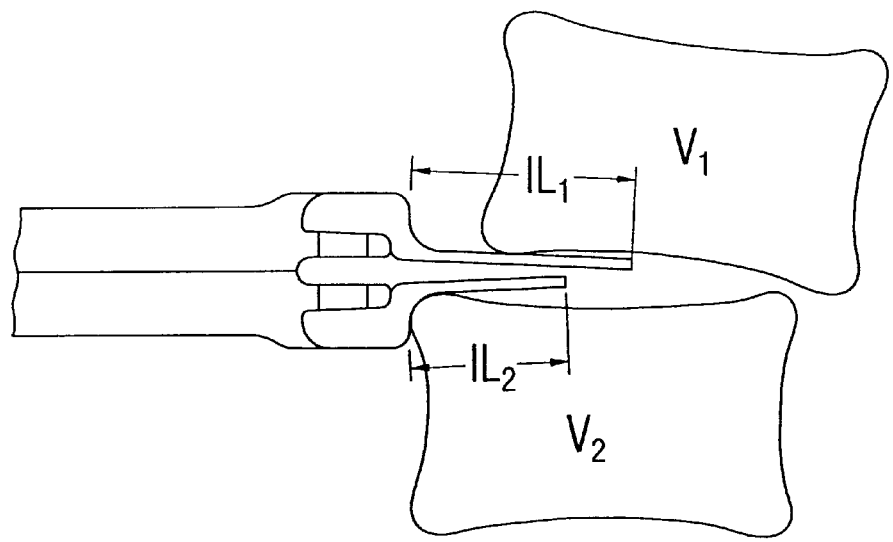
FIG. 10 is a schematic illustration of the distractor of FIG. 1 with blades of different lengths in use.
Figure 11:
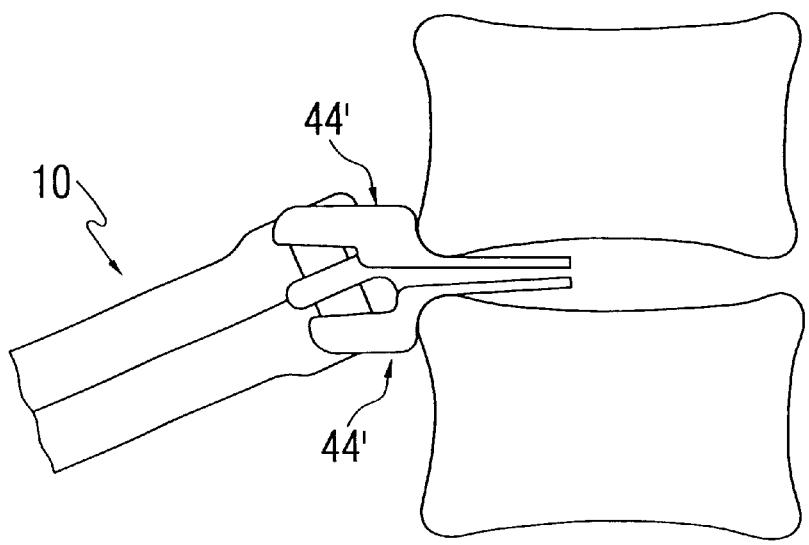
FIG. 11 is a schematic illustration of the distractor of FIG. 1 with blades in use which are positioned at an angle which is not parallel with the distractor mechanism.

Removable attachment of blades 44 to jaws 14 permits a plurality of differently configured blades to be used with distractor 10 depending on the situation or application. For example, the size of the blade may be selected based on the implant to be inserted, different implants potentially having differently sized slots for receiving a distractor blade. The size of the blade may also be selected depending on the size of the vertebrae being treated or the curvature of the vertebral column. For example, it may be desirable to select blades of different insertion lengths $IL_1$, $IL_2$, as shown in FIG. 10, to account for spondylolisthesis which results in one vertebra $V_1$ being closer to the distractor than the other vertebra $V_2$. Blade selection may also depend on the vertebral region being treated, which may affect the difficulty of the approach. For example, in the pelvic region organs and bony structures may complicate insertion and the use of blades 44' which are angled, such as 20°–30°, with respect to the longitudinal axis 31 of distractor mechanism 30 may be desired. Such angled blades 44' would permit an angled approach of distractor 10 to avoid bony structures such as the pelvis.

Figure 12:
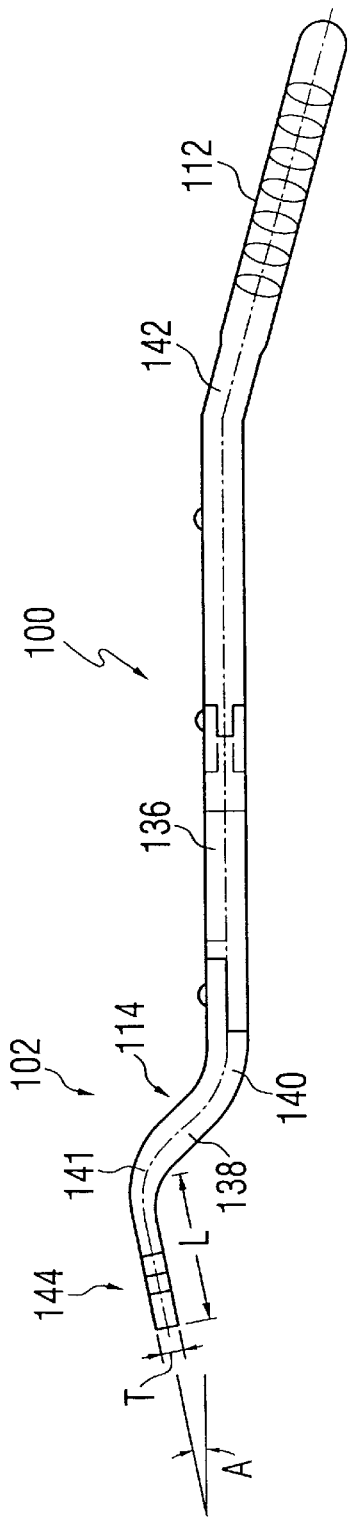
FIG. 12 is a side elevational view of a distractor with curved blades formed in accordance with the principles of the present invention.
Figure 13:
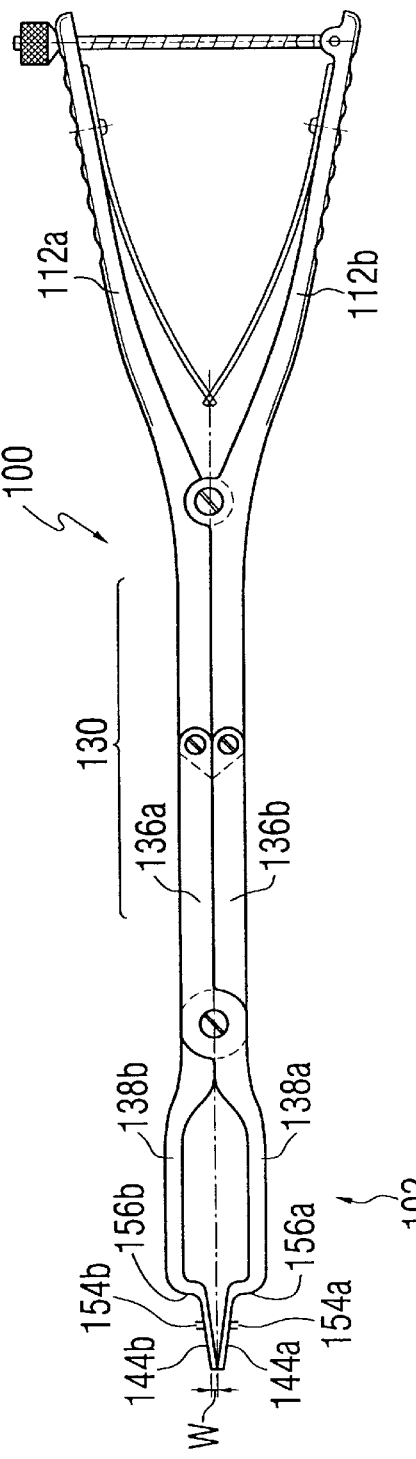
FIG. 13 is a top elevational view of the distractor of FIG. 12.

Although the removability of blades 44 of distractor 10 provides a significant versatility advantage over prior art distractors having blades which are rigidly and fixedly connected to the remaining elements of the distractor, versatility is achievable in accordance with the principles of the present invention in other manners as well. For instance, distal end 102 of distractor 100 of FIGS. 12 and 13 is curved such that blades 144 lie in a plane spaced from the remainder of distractor 100 (i.e., the proximal portions of distractor 100 such as distractor mechanism 130 and handles 112). Such curvature provide several advantages over prior art distractors thus increasing versatility thereof.

For instance, in prior art distractors, the insertion hole commonly is sized to accommodate the distance between spaced apart elements of the distractor. However, the gradual and smooth curvature of jaws 114 and blades 144 permits distractor 100 to be manipulated to fit through the insertion hole such as by "snaking" distractor 100 through. Thus, the curvature of jaws 114 of distractor is selected and configured such that the insertion hole may be sized based on the single element of the distractor with the largest cross-section. Additionally, the curvature of jaws 114 and blades 144 is smooth and selected such that upon insertion, no sharp edges are present which may injure vasculature, organs, etc., along the insertion path. The curvature thus is sufficiently gentle and wide such that jaws 114 and blades 144 are readily manipulated through the patient's body without causing internal injuries or damage. Preferably the curvature has an S-shape to permit such manipulation and rounded surfaces.

In order to provide the above-described curvature in the distal end of distractor 100, a smooth (e.g., radiused without sharp edges) curve 140 which gradually results in distal jaw ends 138 being at an obtuse angle with respect to proximal jaw ends 136 may be provided in jaws 114. Additionally, a similarly smooth and gradual curve 141 preferably is provided between distal jaw ends 138 and blades 144 to result in at least a proximal portion of distractor 100 being in a different plane from that of blades 144 for enhanced visualization as described with respect to bend 40 of distractor 10. Preferably, curve 141 results in an angle A between blades 144 and proximal jaw ends 136 of between 0°–30° and most preferably 10°. A bend 142 may also be provided in handles 112 such that proximal handle ends 118a, 118b are not in the same plane as distal jaw ends 138a, 138b and the distraction site to further enhance visualization, as described above with respect to bend 42 of distractor 10. Bend 142 maybe between 0°–30° and most preferably 15°.

It will be appreciated that distractor mechanism 130 is similar to distractor mechanism 30 and the description of distractor mechanism 30 thus is applicable to distractor mechanism 130 and is not repeated herein. Preferably, if distractor mechanism 130 is similar to distractor mechanism 30, then blades 144a, 144b converge towards each other in a distal direction, as may be appreciated with reference to FIG. 13, as do blades 44 to permit a relative working orientation appropriate for the treatment site, as described above.

Like blades 44 of distractor 10, blades 144a, 144b preferably are closer together than distal jaw ends 138a, 138b, as may be appreciated with reference to FIG. 13, such that blades 144a, 144b securely fit within slots 45 of an implant (as in FIGS. 4 and 5) to grasp the implant yet jaws 114 permit insertion of an implant therethrough. Additionally, vertebral engagers 154a, 154b and transverse engagement walls 156a, 156b, similar to above-described vertebral engagers 54a, 54b and transverse engagement walls 56a, 56b, may be provided to enhance engagement of blades 144a, 144b with the endplates at the treatment site as described above in connection with distractor 10. However, unlike blades 44 of distractor 10, blades 144 of distractor 100 preferably are fixedly secured to jaws 114, such as by formation of blades 144 and jaws 114 as a unitary piece. Thus, distractor 100 may readily be used in severely calcified areas requiring significant strength and durability of the distractor blades.

The dimensions of blades 44a, 44b of distractor 10 and blades 144a, 144b of distractor 100 are preferably similar. The thickness T (FIGS. 8 and 12) of blades 44a, 44b, 144a, 144b (e.g., the working surface, distracting surfaces 52a, 52b) is preferably approximately 2–15 mm and most preferably approximately 6–10 mm. The width W (FIGS. 6 and 13) of blades 44a, 44b, 144a, 144b is preferably approximately 0.5–4 mm and most preferably approximately 1.5–1.8 mm. The length L (FIGS. 6 and 12) of blades 44a, 44b, 144a, 144b is preferably approximately 5–50 mm and most preferably approximately 25–35 mm.

Figure 14:
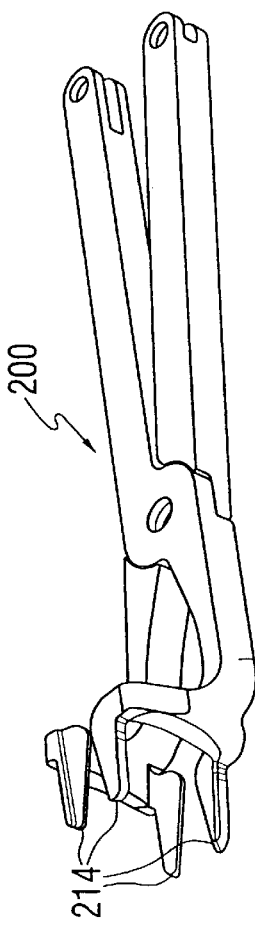
FIG. 14 is a side elevational view of a distractor with a pair of blades coupled to each handle in accordance with the principles of the present invention.
Figure 15:
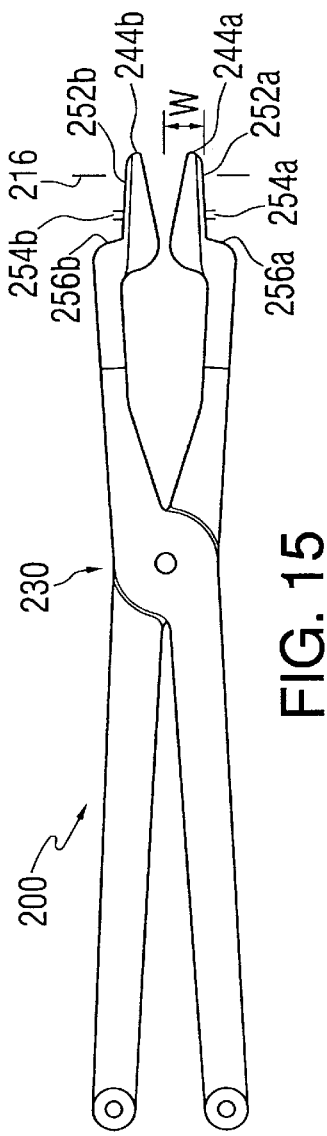
FIG. 15 is a top elevational view of the distractor of FIG. 14.
Figure 16:
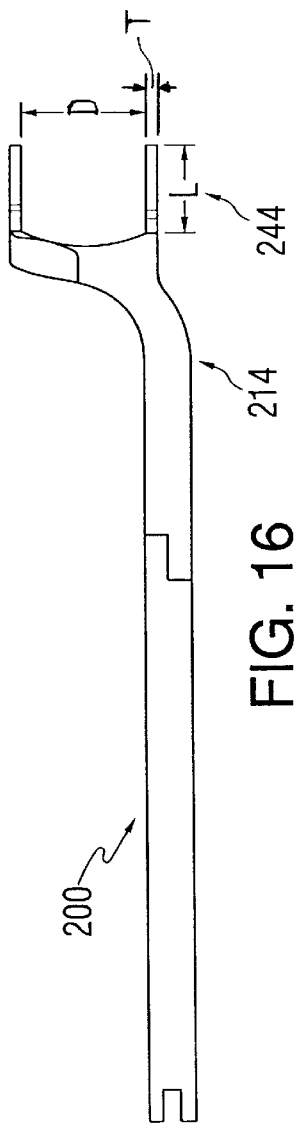
FIG. 16 is a front perspective view of the distractor of FIG. 14.

Versatility of a distractor formed in accordance with the principles of the present invention may alternatively be achieved by the provision of a distractor 200 as shown in FIGS. 14–16 with jaws 214 which permit insertion of any kind of implant, including those not provided with slots as described above with respect to implants 46, 48 of FIGS. 4 and 5. Accordingly, each jaw 214 has a pair of blades 244 sufficiently spaced apart to permit insertion of an implant therebetween without necessarily contacting the implant. Most preferably, blades 244a, 244b are spaced apart a distance D (FIG. 16) to permit insertion of an implant with a medial-lateral width and/or an anterior-posterior width of at least 50% of the corresponding dimension (i.e., medial-lateral or anterior-posterior) of the endplates between which the implant is to be inserted.

As may be appreciated upon comparison of FIGS. 12 and 13, blades 244 have a width W along distraction axis 216 greater than thickness T perpendicular to distraction axis 216 (along the working surface). Such dimension minimizes distracting surfaces 252a, 252b to minimize the surface of the endplates contacted by blades 244 and to permit sufficient space for insertion of an implant between blades 244. Thus, contact thickness T of distracting surfaces 252a, 252b is selected to be as small as possible (such that a minimum amount of annulus need be removed and a sufficient amount of space is provided for the insertion of an implant between blades 244a, 244b) while still permitting safe distraction of adjacent vertebrae without causing damage thereto. Additionally, the width W of blades 244 along distraction axis 216 preferably is selected to ensure the strength of blades 244 so that blades 244 do not deform or buckle during distraction despite the relatively small thickness T of distracting surfaces 252a, 252b. Preferred dimensions are approximately 3–15 mm (most preferably approximately 7–10 mm) for width W and approximately 0.5–8 mm (most preferably approximately 1.5–3 mm) for thickness T. Because of such dimensions, blades 244a, 244b preferably overlap one another when distractor mechanism 230 is in a neutral configuration (with blades 244a, 244b are in their closest relative positions), thereby minimizing the space along distraction axis 216 occupied by blades 244a, 244b and the size of the insertion path necessary for insertion of blades 244 into the treatment site. The length L of blades 244, like length L of blades 44 and 144, is preferably approximately 5–50 mm and most preferably approximately 25–35 mm.

Vertebral engagers 254a, 254b and transverse engagement walls 256a, 256b, similar to above-described vertebral engagers 54a, 54b and transverse engagement walls 56a, 56b, may be provided to enhance engagement of blades 244a, 244b with the endplates at the treatment site as described above in connection with distractor 10. Blades 244 of distractor 200 preferably are fixedly secured to jaws 214, such as by formation of blades 244 and jaws 214 as a unitary piece. Thus, distractor 200 may readily be used in severely calcified areas requiring significant strength and durability of the distractor blades.

It will be appreciated that distractor mechanism 130 is similar to distractor mechanism 30 and the description of distractor mechanism 30 thus is applicable to distractor mechanism 130 and is not repeated herein.

It will also be appreciated that distractor mechanism 230 of distractor 200 may be a simple scissors configuration with handles 212 and jaws 214 formed along the same lever element, as may be appreciated with reference to FIGS. 12 and 14. However, distractor mechanism 230 may instead have substantially the same configuration as distractor mechanism 30 of distractor 10 or distractor mechanism 130 of distractor 100. The description of distractor mechanism 30 thus is applicable to distractor mechanism 230 and is not repeated herein. Conversely, it will be appreciated that distractor mechanism 30 or distractor mechanism 130 may have substantially the same configuration as distractor mechanism 230. Preferably, if distractor mechanism 230 is either scissors-type configuration (single scissors as in FIGS. 12–14 or double-scissors as in distractor mechanisms 30 and 130), then blades 244 converge towards each other in a distal direction as do blades 44 to permit a relative working orientation appropriate for the treatment site, as described above.

While the foregoing description and drawings represent the preferred embodiments of the present invention, it will be understood that various additions and/or substitutions may be made therein without departing from the spirit and scope of the present invention as defined in the accompanying claims. One skilled in the art will appreciate that the invention may be used with many modifications of structure, forms, arrangement, proportions, materials, and components and otherwise, used in the practice of the invention and which are particularly adapted to specific environments and operative requirements, without departing from the principles of the present invention. The presently disclosed embodiments are therefore to be considered in all respects as illustrative and not restrictive, the scope of the invention being indicated by the appended claims, and not limited to the foregoing description.

What is claimed is:

1. A distractor comprising:

first and second bandies defining a first longitudinal axis;

first and second jaws respectively associated with said first and second handles;

first and second blades respectively associated with said first and second jaws; and a distractor mechanism coupled between said handles and said jaws such that movement of said handles actuates said distractor mechanism to move said jaws apart along a second axis substantially perpendicular to the first longitudinal axis;

wherein at least one jaw includes a mating fixture defining a third axis substantially perpendicular to a plane defined by the first and second axes, and at least one of said blades is formed with a mating portion configured for removable association with said mating fixture substantially along the third axis.

2. The distractor of claim 1, wherein each jaw includes a mating fixture in the form of a mounting socket and each blade includes a mating portion in the form of a mounting post shaped for removable association with said mounting socket of each jaw.

3. The distractor of claim 2, wherein each blade post is rotatably positioned within each mounting socket to selectively position the blades relative to one another.

4. The distractor of claim 3, further comprising a locking mechanism for locking the position of each blade post within its respective socket.

5. The distractor of claim 4, wherein the locking mechanism includes a ball detent.

6. The distractor of claim 1, wherein each blade mating portion is movably associated with each mating fixture when associated therewith to selectively position the blades relative to the jaws.

7. The distractor of claim 1, further comprising a locking mechanism for locking the mating portion in association with the mating fixture.

8. The distractor of claim 1, wherein the first and second blades extend at first and second angles relative tote first and second jaws.

9. The distractor of claim 8, wherein the first and second angles range from about 20° to 30° relative to a longitudinal axis of the distractor mechanism.

10. The distractor of claim 1, wherein the first blade has an insertion length and the second blade has an insertion length, and the insertion length of the first blade is different from the insertion length of the second blade.

11. The distractor of claim 1, wherein the first and second blades include at least one curved portion.

12. The distractor of claim 1, wherein the first and second jaws include at least one curved portion.

13. The distractor of claim 1, wherein the first and second blades each comprise a pair of spaced apart blades to contact anatomical elements to be distracted and permit insertion of an implant between said first and second blades and said anatomical elements.

14. The distractor of claim 1, wherein the first and second jaws are removably associated with the first and second handles.

15. A distractor comprising:

first and second handles defining a first longitudinal axis;

first and second jaws respectively associated with said first and second handles; and a distractor mechanism coupled between said bandies and said jaws such that movement of said handles actuates said disfractor mechanism to move said jaws apart alone a second axis substantially perpendicular to the first longitudinal axis;

wherein at least one of the first and second handles includes a mating fixture defining a third axis substantially perpendicular to a nine defined by the first and second axes, and at least one of said first and second jaws is formed with a mating portion configured for removable association with said mating fixture substantially along the third axis.

16. The distractor of claim 15, wherein the mating fixture is a mounting socket and the mating portion is a mounting post configured for removable association with said mounting sockets.

17. The distractor of claim 16, wherein each mounting post is rotatably positionable within each mounting socket to selectively position the jaws relative to one another.

18. The distractor of claim 17, further comprising a locking mechanism for locking the position of each mounting post within its respective socket.

19. The distractor of claim 18, wherein the locking mechanism includes a ball detent.

20. The distractor of claim 15, further comprising a locking mechanism for looking the mating portion in association with the mating fixture.

21. The distractor of claim 15, wherein the first jaw has an insertion length and the second jaw has an insertion length, and the insertion length of the first jaw is different from the insertion length of the second jaw.

22. The distractor of claim 15, wherein the first and second jaws include at lest one curved portion.

23. A distractor comprising:

first and second handles defining a first longitudinal axis;

first and second jaws respectively removably associated with said first and second handles;

a distractor mechanism coupled between said handles and said jaws such that movement of said handles actuates said distractor mechanism to move said jaws apart along a second axis substantially perpendicular to the first longitudinal axis; and wherein the first and second laws are removably associated with the first and second handles substantially along a third axis perpendicular to a plane defined by the first and second axes.

24. A distractor comprising:

a proximal end having first and second handles located in a first plane;

first and second jaws respectively associated with said first and second handles, said first and second jaws located in a second plane different from the first;

first and second blades respectively associated with said first and second jaws; and a distractor mechanism coupled between said handles and said jaws such that movement of said handles actuates said distractor mechanism to move said jaws apart; and wherein the first plane is misled with respect to the second plane so as to permit visualization of the blades from the proximal end.

25. The distractor of claim 24, wherein at least one jaw includes a mating fixture defining an axis substantially perpendicular to the second plane, and at least one of said blades is formed with a mating portion configured for removable association with said mating fixture substantially along said axis.

26. The distractor of claim 24, wherein each jaw includes a mating fixture in the form of a mounting socket and each blade includes a mating portion in the form of a mounting post shaped for removable association with said mounting socket of each jaw.

27. The distractor of claim 26, wherein each blade mating portion is movably associated with each mating fixture when associated therewith to selectively position the blades relative to the jaws.

28. The dish-actor of claim 24, wherein the first plane mid the second plane form an angle therebetween ranging from about 5° to about 30°.

29. The distractor of claim 28, wherein the angle ranges from about 5° to about 20°.

30. The distractor of claim 28, wherein the angle is substantially 15°.

\* \* \* \* \*